United States Patent
Bergquist

(10) Patent No.: US 6,723,330 B2
(45) Date of Patent: Apr. 20, 2004

(54) POWDERED COMPOSITION FOR COSMETIC EFFERVESCENT CLEANSING PILLOW

(75) Inventor: Paul Roland Bergquist, Southport, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 130 days.

(21) Appl. No.: 10/156,914

(22) Filed: May 29, 2002

(65) Prior Publication Data

US 2003/0059387 A1 Mar. 27, 2003

Related U.S. Application Data

(60) Provisional application No. 60/318,701, filed on Sep. 13, 2001.

(51) Int. Cl.⁷ .............................. A61K 6/00; A61K 7/00; A61K 9/00; A61K 25/34

(52) U.S. Cl. ..................... 424/402; 424/400; 424/401

(58) Field of Search ................................ 424/402, 400, 424/401

(56) References Cited

U.S. PATENT DOCUMENTS 6,063,390 A * 5/2000 Farrell et al. ............... 424/404
6,313,086 B1 11/2001 Askew et al. ............... 510/478

* cited by examiner

Primary Examiner—Thurman K. Page
Assistant Examiner—S. Howard

(57) ABSTRACT

An article for cleansing body surfaces is provided which includes an effervescent cleansing composition capable of generating a foam upon contact with water and a pouch for housing the composition. The composition is a substantially dry flowable powder which includes an alkaline material, an acid, and a particulate composition, the latter pre-formed as a carrier solid of surface area greater than 10 $m^2/g$ onto which is absorbed at least one liquid or semi-liquid skin benefit agent. Calcium silicate is particularly useful as a carrier solid.

7 Claims, No Drawings

POWDERED COMPOSITION FOR COSMETIC EFFERVESCENT CLEANSING PILLOW

This application claims the benefit of Provisional application No. 60/318,701 filed Sep. 13, 2001.

BACKGROUND OF THE INVENTION

1. Field of the Invention

The invention concerns a substantially dry flowable powder composition for use in a cleansing article. More specifically, the article is a water-insoluble sachet retaining the powder which upon being actuated with water provides an effervescent foam passing through the sachet walls.

2. The Related Art

Cleansing products have traditionally been marketed in the form of bar soaps, shower gels and mousses, the lather being generated by mechanical and aerosol dispensers. Mechanical implements have been used by consumers to assist in lather formation and physical removal of dirt through scrubbing. Wash cloths have been the implement of choice throughout recent history.

New formats for cleansing hold great consumer appeal. For instance, surfactant and conditioner compositions have been layered into apertured wipes such as disclosed in U.S. Pat. No. 6,280,757 (McAtee et al.). Open-mesh sponges such as described in U.S. Pat. No. 6,066,607 (Gordon et al.) have assisted in generating foam from shower gets thereby improving speed and quality of lathering.

U.S. Pat. No. 5,980,931 (Fowler et al.) describes a substantially dry, disposable personal care article wherein a surfactant system is dried onto a water-insoluble non-woven or similar substrate. A second generation of dual layered towelette has been reported. See WO 00/42961 (Smith), WO 01/08542 (Cen et al.), WO 01/08640 (Smith et al.), WO 01/08641 (Lorenzi et al.), WO 01/08655 (Phipps et al.), WO 01/08656 (Lorenzi et al.), WO 01/08657 (Lorenzi et al.) and WO 01/08658 (Cawkwell et al.) all describing disposable personal cleansing towelettes with lathering surfactant on at least a two layer cloth with one layer being a high loft substrate. Consumers are expected to place the towelette under water to generate a surfactant lather.

Another approach is described in U.S. Pat. No. 6,063,390 (Farrell et al.) which discloses wiping articles that include an effervescent, preferably powdered, cleanser composition held within a pouch of a sachet. Water contact causes the composition to effervesce. Several problems exist with the aforedescribed "pillow" system.

Not all components of the effervescent cleanser composition are powders. Some essential components may only be available as liquids or pastes. The compositions formulated with these materials would themselves exhibit tackiness becoming poorly flowable and/or agglomerating into an uncontrolled particle size distribution. Transport through manufacturing equipment and precise delivery of a powder charge into individual sachets can thereby become a significant problem.

Accordingly, it is an object of the present invention to provide a sachet with an effervescent powdered composition that may contain liquids and/or paste components yet exhibit good powder flowability and minimum agglomeration.

Another object of the present invention is to provide a sachet filled with an effervescent powdered composition wherein any liquids and/or paste components are compounded with powdered solid components in a manner exhibiting no stickiness and avoiding liquid exudation upon storage of the powdered composition.

These and other objects of the present invention will become more fully apparent from consideration of the following summary and detailed discussion.

SUMMARY OF THE INVENTION

A cosmetic article is provided for cleansing body surfaces, the article including:

an effervescent cleansing composition which is a substantially dry flowable powder the composition including:
  (i) from about 1 to about 80% of an alkaline material;
  (ii) from about 0.5 to about 80% of an acid material; and
  (iii) from about 0.1 to about 60% of a flowable particulate powder including:
    a) a powdered carrier having a surface area greater than about 10 $m^2/g$; and
    b) at least one skin benefit agent of softening point less than 30° C. absorbed onto the carrier;

a pouch formed of first and second water insoluble substrates, at least one being water permeable, the first and second water-insoluble substrates forming therebetween an area housing the effervescent cleansing composition.

DETAILED DESCRIPTION OF THE INVENTION

The present invention provides for a substantially dry flowable powder that can be utilized with the sachets for delivering an effervescent cleansing system upon contact with water. Liquid and semi-liquid or pasty components are pre-absorbed onto a carrier solid having a surface area greater than about 10 $m^2/g$. Thereafter the resultant particulate composition can be combined with other normally solid powders such as sodium bicarbonate and dry acid such as citric acid.

A first component of compositions within the pouch is that of an acidic material. Suitable for this purpose are any acids present in dry solid form. Especially appropriate are $C_2$–$C_{20}$ organic mono- and poly-carboxylic acids and especially alpha- and beta-hydroxycarboxylic acids; $C_2$–$C_{20}$ organophosphorus acids such as phytic acid; $C_2$–$C_{20}$ organosulfur acids such as toluene sulfonic acid; and peroxides such as hydrogen peroxide. Typical hydroxycarboxylic acids include adipic, glutaric, succinic, tartaric, malic, maleic, lactic, salicylic and citric acids as well as acid forming lactones such as gluconolactone and glucarolactone. Most preferred is citric acid. Also suitable as acid material are water soluble synthetic or natural polymers such as polyacrylates (e.g. encapsulating polyacrylic acid), cellulosic gums, polyurethane and polyoxyalkalene polymers. By the term "acid" is meant any substance which when dissolved in deionized water at 1% concentration will have a pH of less than 7, preferably less than 6.5, optimally less than 5. These acids preferably at 25° C. are in solid form, i.e. having melting points no less than 25° C. Concentrations of the acid should range from about 0.5 to about 80%, preferably from about 10 to about 65%, optimally from about 20 to about 45% by weight of the total composition.

A second essential component of compositions within the pouch is that of an alkaline material. The alkaline material is a substance which can generate a gas such as carbon dioxide, nitrogen or oxygen, i.e. effervesce, when contacted with water and the acidic material. Suitable alkaline materials are anhydrous salts of carbonates and bicarbonates, alkaline peroxides (e.g. sodium perborate and sodium percarbonate) and azides (e.g. sodium azide). Preferably the alkaline material is sodium or potassium bicarbonate. Amounts of the alkaline material may range from about 1 to about 80%, preferably from about 5 to about 49%, more preferably from about 15 to about 40%, optimally from about 25 to about 35% by weight of the total composition.

By the term "anhydrous" is meant the presence of no more than 5%, preferably no more than 3.5% and optimally no more than 1% water by weight of the total composition. Water of hydration is not considered to be water for purposes of the anhydrous definition. However, it is preferred to minimize, preferably to eliminate any water of hydration.

Advantageously the combined amount of acidic and alkaline materials will be at least about 1.5%, preferably from about 40 to about 95%, optimally from about 60 to about 80% by weight of the total composition.

A third component of compositions within the pouch will be a particulate composition. This will include a carrier solid having a surface area greater than about 10 $m^2/g$, preferably greater than 50 $m^2/g$ and optimally greater than 100 $m^2/g$ as measured by the BET Surface Area procedure. Generally the preferred surface area should range from about 150 to about 1,000 $m^2/g$.

Carrier solids may include aluminas, silicas, calcium silicate, aluminum silicate, aluminum magnesium silicate, clays (e.g. hectorite, bentonite and laponite), Fuller's Earth, zeolite and combinations thereof. Median particle sizes may range from about 0.1 micron to about 200 micron, preferably from about 1 micron to about 100 micron, optimally from about 5 micron to about 50 micron. Most preferred is synthetic calcium silicate which is available as Micro-Cel® C from the Celite Corporation and Hubersorb® 600 from the J. M. Huber Corporation. Amounts of these inorganic carrier solids may range from about 1 to about 50%, preferably from about 3 to about 30%, optimally from about 5 to about 15% by weight of the total flowable effervescent cleansing composition.

Liquids and semi-solids (i.e. pastes), especially skin benefit agents, are pre-absorbed onto the carrier solid. By the term "liquid" is meant any component which has a melting point below 30° C., preferably below 15° C. The term "semi-solid" is meant to encompass any sticky, poorly flowing pasty component which has a softening point below about 30° C. Typically effervescent systems of the present invention may contain a liquid or a semi-liquid skin benefit agent in an amount from about 0.01 to about 50%, preferably from about 0.5 to about 25%, optimally from about 1 to about 10% by weight of the total flowable effervescent cleansing composition.

In the prior art, components which were solid, liquid and semi-solid were all formulated together without any regard to appropriate mixing sequence. For this invention, the liquid and semi-liquid skin benefit agents are first pre-absorbed onto the carrier solid to form a particulate composition to result in a freely flowing powder. Once the powder is pre-formed, this material can be blended with the alkaline and acid solids, as well as any other powdered components of the total composition.

In another aspect of the present invention it is desirable to employ a skin benefit agent that may gel upon contact with carrier solids. Gelation inhibits the de-absorption of liquids and semi-solids from the carrier. Gels may be formed by such materials as acyloyl lactylates, although the invention is not so limited. Representative lactylates include sodium lauroyl lactylate and sodium stearoyl lactylate, available respectively as Pationic® 138C and Pationic® SSL from Rita Corporation.

An optional but desirable component of compositions according to the present invention is that of a surfactant, especially dry surfactant solids at 20° C. Surfactants may be of the anionic, cationic, nonionic, amphoteric, zwitterionic varieties and combinations thereof. Illustrative surfactants are sodium cocoyl isethionate, sodium methyl cocoyl taurate, sodium lauryl sulphate, sodium lauryl sulfoacetate, sodium $C_{14}$–$C_{16}$ olefin sulfonate and combinations thereof.

Amounts of the surfactant may range from about 0.1 to about 30%, preferably from about 1 to about 20%, optimally from about 5 to about 15% by weight of the total composition.

A variety of skin benefit agents are included to improve afterfeel properties. Some of these agents may be in the aforementioned liquid or semi-liquid state and others may be solid flowable powders. Within the skin benefit agent scope are several categories of materials. These include emollients, antiaging actives, antibacterials and fungicides, skin lighteners, sunscreens and combinations thereof.

Emollients may be in the form of natural or synthetic esters, silicone oils, hydrocarbons, starches, fatty acids and mixtures thereof. Typically the emollient may range in concentration from about 0.1 to about 35% by weight of the total composition.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 26 carbon atoms. Examples thereof include isoarachidyl neopentanoate, isononyl isonanonoate, oleyl myristate, oleyl stearate, oleyl oleate and isocetyl behenate.

(2) Ether-esters such as fatty acid esters of ethoxylated fatty alcohols.

(3) Polyhydric alcohol esters. Ethylene glycol mono and di-fatty acid ester, diethylene glycol mono- and di-fatty acid esters, polyethylene glycol (200–6000) mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate and arachidyl behenate.

(5) Sterols esters, of which cholesterol fatty acid esters are examples thereof.

(6) Triglycerides such as sunflower seed oil, maleated sunflower seed oil, borage seed oil, polycottonseedate oil and safflower oil.

Hydrocarbons suitable as emollients include petrolatum, mineral oil, isoparaffins and hydrocarbon waxes such as polyethylene.

Starches are also suitable emollients. Typical of this class is tapioca and arabinogalactan.

Fatty acids may also be suitable as emollients. The fatty acids normally have from 10 to 30 carbon atoms. Illustrative of this category are pelargonic, lauric, myristic, palmitic, stearic, isostearic, hydroxystearic, oleic, linoleic, riconleic, arachidic, behenic and erucic acids.

Antiaging actives are useful as skin benefit agents. Included within this category are vitamins, retinoids and combinations thereof. Amounts of these materials may range from about 0.0001 to about 20% by weight of the total composition. Suitable vitamins include ascorbic acid, Vitamin $B_6$, Vitamin $B_{12}$, tocopherol as well as salts and $C_1$–$C_{20}$ esters thereof. Suitable retinoids include retinoic acid as well as its $C_1$–$C_{22}$ esters and salts, retinol and $C_1$–$C_{22}$ fatty esters of retinol including retinyl linoleate.

Another class of antiaging actives are the alpha- and beta-hydroxycarboxylic acids and salts thereof. Representative of this group are glycolic acid, lactic acid, malic acid, hydroxyoctanoic acid and mixtures of these as well as their salts. Suitable salts are the alkalimetal, ammonium and $C_1$–$C_{10}$ alkanol ammonium salts.

Antibacterials and fungicidals may be included as skin benefit agents. Representative of these categories are triclosan, tricloban, hexetidene, chlorhexadene, gluconates, zinc salts (e.g. zinc citrate and zinc phenolsulfonate) and combinations thereof.

Skin tighteners may also be included under the skin benefit agents. Typical of this category are niacinamide, kojic acid, arbutin, vanillin, ferulic acid and esters thereof, resorcinol, hydroquinone, placental extract and combinations thereof.

Sunscreens may be included as skin benefit agents. Particularly preferred are such materials as ethylhexyl p-methoxycinnamate, available as Parsol® MCX, and benzophenone-3, also known as Oxybenzone. Amounts of the sunscreen agents will generally range from 0.1 to 30%, preferably from 2 to 20%, optimally from 4 to 10% by weight.

Adjunct functional agents may also be incorporated into compositions of the present invention. These include electrolytes, thickeners and mixtures thereof. Amounts of these substances may range from about 0.1 to about 20%, preferably from about 0.3 to about 10%, optimally between about 0.5 and about 5% by weight of the total composition.

Electrolytes may be selected from alkali, alkaline earth or ammonium salts of phosphates, silicates, halides, sulphates and mixtures thereof. Typical phosphates are potassium polymetaphosphate, sodium tripolyphosphate, sodium tetrapyrophosphate, sodium or potassium pyrophosphate and sodium hexametaphosphate. Most preferred is potassium polymetaphosphate available as Lipothix 100B® which is a 70:30 mixture of potassium polymetaphosphate and sodium bicarbonate, available from Lipo Chemicals, Inc., Paterson, N.J. Preferred sulphates are the magnesium sulphates.

Thickeners which may improve afterfeel properties on skin include inorganic or organic substances. A particularly preferred inorganic thickener is sodium magnesium silicate commercially available as Optigel SH®. Organic thickeners include alginic acid as well as sodium and calcium alginates, sodium carboxymethyl cellulose, hydroxypropyl methylcellulose, hydroxypropyl cellulose, hydroxyethyl cellulose and combinations thereof. Most preferred is alginic acid commercially available as Kelacid® from Sud-Chemie Rheologicals, Louisville, Ky. Alginic acid is highly effective at removing the slimy feel associated with deposits of alkaline material which are not fully rinsed away from the skin. Amounts of the thickener may range from about 0.1 to about 20%.

Polysaccharides useful in this invention are dry solid anhydrous substances such as sorbitol, sugars, (such as trehalose) starches, modified starches (e.g. aluminum octenyl succinate) and mixtures thereof. Most preferred is sorbitol.

Deposition aids may also be incorporated in compositions of the present invention. These assist in depositing skin benefit agents onto the skin. Particularly effective are cationic monomers and polymers for this purpose. Illustrative but not limiting examples include Polyquaternium-7 (available as Merquat® 2200) and cationic guar gums such as guar hydroxypropyltrimonium chloride (available as Jaguar® C13S). Amounts of the deposition aid may range from about 0.01 to about 2%, preferably from about 0.05 to about 0.5%, optimally from about 0.1 to about 0.3% by weight.

Preservatives can desirably be incorporated into the cosmetic compositions of this invention to protect against the growth of potentially harmful microorganisms. Suitable traditional preservatives for compositions of this invention are alkyl esters of para-hydroxybenzoic acids. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the sue of the composition and possible incompatibilities between the preservatives and other ingredients in the emulsion. Preservatives are preferably employed in amounts ranging from 0.01% to 2% by weight of the composition.

Colorants may also be included in compositions of the present invention. These substances may range from about 0.05 to about 5%, preferably between 0.1 and 3% by weight.

Effervescent cleansing compositions of this invention will be placed within a pouch formed between a first and second water-insoluble substrate sheet, preferably at least one of these being a flexible sheet. At least one of the sheets must be water permeable, most preferably both sheets should have water permeability. For definitional purposes, first and second sheets can be folded-over panels of a single unitary sheet. Alternatively the pouch can be formed of two different substrates for each of the outer walls, one may be formed of a hi-loft and the other of a lo-loft fabric. Suitable materials for forming sheets may be rayon, polyester, polyethylene, polypropylene, cotton or any combination thereof. These sheets may be woven or non-woven. Most preferred is a non-woven rayon. Cellulosic paper fiber substrates are best not employed because of their insufficient wet-strength although they may be blended with other fibers referenced above; it is important that the substrate sheets are not readily torn open through consumer rubbing of the article.

Skin surfaces against which articles of the present invention are useful include face, body, scalp, axilla and even legs/feet. When the article is a foot cleanser, it would be advantageous for the pouch on one of its sides to be coarse while the second of the sheets may be soft and gentle. An abrasive non-woven flexible sheet in a foot cleanser product is useful for rubbing against calluses while the second sheet of the pouch remains smooth.

It is important that the substrate sheets are not readily torn open through consumer rubbing of the article. Unlike laundry sachet articles, pouches of the present invention should not rupture to allow dispersion of their granular contents into wash water. Rather it is intended for all composition components to exit by dissolution through the permeable walls of the pouch.

Articles according to the present invention may be formed in the following manner. A powdered carrier of high surface area is charged to a milling vessel. Liquid or semi-solid skin benefit agents are sprayed onto the carrier. The combination is agitated to thoroughly intermix carrier and agent thereby achieving uniformly distributed absorption. The resultant free flowing powder is charged along with other constituents of the effervescent cleansing composition into a larger dry mill or similar apparatus and blended until a uniformly distributed powder results.

Rolls of first and second substrate sheets are unwound from different sides of a charging position. The effervescent cleansing composition is placed into a hopper positioned over the charging position and between the substrate sheets. A discrete charge of powdered composition is released directly between the sheets and caught in a partially formed pillow. At this point all edges defining the pouch are sealed in register trapping the effervescent cleansing composition within. Cutters then separate one sealed section from another thereby forming the article. One or more of the articles are then packaged within a moisture impermeable outer package such as a laminated foil bag to prevent activation of the effervescent system during storage.

Ultrasonic welding may be employed as an alternative to heat-sealing of the first and second substrates together. Thread stitching, glue application or other closure mechanisms may also be utilized.

Except in the operating and comparative examples, or where otherwise explicitly indicated, all numbers in this description indicating amounts of material are to be understood as modified by the word "about".

The term "comprising" is meant not to be limiting to any subsequently stated elements but rather to encompass non-specified elements of major or minor functional importance. In other words the listed steps, elements or options need not be exhaustive.

The following examples will more fully illustrate embodiments of this invention. All parts, percentages and proportions referred to herein and in the appended claims are by weight unless otherwise indicated.

EXAMPLE

An effervescent cleansing composition was formulated according to the components reported in Table I.

TABLE I

| INGREDIENT | WEIGHT % |
| --- | --- |
| Anhydrous Citric Acid | 24.00 |
| Sodium Bicarbonate | 24.00 |
| Sodium Lauryl Sulfoacetate | 3.75 |

TABLE I-continued

| INGREDIENT | WEIGHT % |
| --- | --- |
| Sodium Cocoyl isethionate | 3.75 |
| Polyquaternium 7 | 0.50 |
| Sodium C14–C16 Olefin Sulfonate | 3.75 |
| Guar hydroxypropyltrimonium Chloride | 0.40 |
| Ascorbyl Palmitate | 0.01 |
| Isocetyl Behenate | 5.00 |
| Sodium Stearoyl Lactylate | 3.00 |
| Disodium Dimethicone Copolyol Sulfosuccinate | 1.00 |
| Vitamin A Palmitate | 0.01 |
| Sodium Lauroyl Lactylate | 5.00 |
| PEG 8000 | 5.00 |
| Vitamin E | 0.40 |
| Calcium Silicate | 9.00 |
| Maltodextrin | 11.13 |
| Fragrance | 0.30 |

As a first step in the preparation, calcium silicate was mixed with the liquid and semi-liquid materials of sodium stearoyl lactylate and sodium lauroyl lactylate. Both lactylates were first dissolved in isocetyl behenate. The behenate solution was heated to 40–80° C. prior to application onto the calcium silicate carrier. The mixture was then agitated in a reactor. Thereafter, fragrance oil and Vitamin A palmitate was introduced into the silicate mixture.

The resultant pre-mix of calcium silicate was then fed into a second blending drum containing the other powdered components including anhydrous citric acid, sodium carbonate, maltodextrin and the remaining surfactants/skin conditioners.

A final composition was achieved which was a blended dry flowable powder. The final powder was transferred to a hopper for distribution of charge to each sachet. In this process, 3.5 grams of the dry mixed ingredients are dosed into an oval pouch of major and minor elliptical axis of 9 cm and 5.5 cm length. The powdered sample is placed between a layer of spun lace substrate and a spunbond/meltblown/spunbond (SMS) layer to which a high loft sheet was sealed. All sides of the pouch were welded by ultrasonic heat to ensure against powder escaping.

The foregoing description and drawing illustrate selected embodiments of the present invention. In light thereof, variations and modifications will be suggested to one skilled in the art, all of which are within the spirit and purview of this invention.

What is claimed is:

1. A cosmetic article for cleansing body surfaces, the article comprising:
   an effervescent cleansing composition which is a substantially dry flowable powder the composition comprising:
   (i) from about 1 to about 80% of an alkaline material;
   (ii) from about 0.5 to about 80% of an acid material; and
   (iii) from about 0.1 to about 60% of a flowable particulate powder comprising:
      a) a powdered carrier having a surface area greater than about 10 m$^2$/g; and
      b) at least one skin benefit agent of softening point less than 30° C. absorbed onto the carrier;
   a pouch formed of first and second water insoluble substrates, at least one being water permeable, the first and second water-insoluble substrates forming therebetween an area housing the effervescent cleansing composition.

2. The article according to claim 1 wherein the skin benefit agent is a substance which gels upon contact with the powdered carrier.

3. The article according to claim 2 wherein the gel forming skin benefit agent is an acyloyl lactylate.

4. The article according to claim 1 wherein the carrier solid is a calcium salt.

5. The according to claim 4 wherein the calcium salt is calcium silicate.

6. The article according to claim 1 wherein the surface area of the carrier ranges from about 150 to about 1,000 $m^2/g$.

7. A cosmetic article for cleansing body surfaces, the article comprising:
    an effervescent cleansing composition which is a substantially dry flowable powder the composition comprising:
        (i) from about 1 to about 80% of an alkaline material;
        (ii) from about 0.5 to about 80% of an acid material; and
        (iii) from about 0.1 to about 60% of a flowable particulate powder comprising:
            a) a powdered carrier which is a calcium silicate having a surface area greater than about 10 $m^2/g$; and
            b) at least one skin benefit agent of softening point less than 30° C. absorbed onto the carrier;
a pouch formed of first and second water insoluble substrates, at least one being water permeable, the first and second water-insoluble substrates forming therebetween an area housing the effervescent cleansing composition.

* * * * *